(12) United States Patent
Kimura

(10) Patent No.: US 10,702,502 B2
(45) Date of Patent: *Jul. 7, 2020

(54) INHIBITOR FOR RETINOCHOROIDAL DISORDERS

(71) Applicant: Yamaguchi University, Yamaguchi (JP)

(72) Inventor: Kazuhiro Kimura, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/892,536

(22) PCT Filed: May 21, 2014

(86) PCT No.: PCT/JP2014/002667
§ 371 (c)(1),
(2) Date: Nov. 19, 2015

(87) PCT Pub. No.: WO2014/188716
PCT Pub. Date: Nov. 27, 2014

(65) Prior Publication Data
US 2016/0120843 A1 May 5, 2016

(30) Foreign Application Priority Data
May 22, 2013 (JP) ................. 2013-107706

(51) Int. Cl.
| | | |
|---|---|---|
| A61K 31/415 | (2006.01) | |
| A61K 9/06 | (2006.01) | |
| A61K 9/08 | (2006.01) | |
| A61K 9/00 | (2006.01) | |
| A61K 47/44 | (2017.01) | |
| A61K 47/26 | (2006.01) | |
| A61K 9/20 | (2006.01) | |

(52) U.S. Cl.
CPC .......... *A61K 31/415* (2013.01); *A61K 9/0048* (2013.01); *A61K 9/06* (2013.01); *A61K 9/08* (2013.01); *A61K 9/205* (2013.01); *A61K 9/2018* (2013.01); *A61K 47/26* (2013.01); *A61K 47/44* (2013.01)

(58) Field of Classification Search
USPC ........................................... 514/406
See application file for complete search history.

(56) References Cited

U.S. PATENT DOCUMENTS

| | | | |
|---|---|---|---|
| 5,624,957 A | 4/1997 | Swann et al. | |
| 5,760,084 A | 6/1998 | Swann et al. | |
| 5,824,685 A * | 10/1998 | Campochiaro | A61K 31/192 514/277 |
| 6,187,950 B1 | 2/2001 | Song et al. | |
| 6,204,288 B1 | 3/2001 | Pershadsingh et al. | |
| 6,313,168 B1 | 11/2001 | Pacifici et al. | |
| 6,777,418 B2 | 8/2004 | Lapierre et al. | |
| 6,838,472 B2 | 1/2005 | Klaus et al. | |
| 6,844,466 B2 | 1/2005 | Belloni et al. | |
| 7,345,931 B2 | 3/2008 | Partsch et al. | |
| 7,547,687 B2 | 6/2009 | Reading et al. | |
| 9,314,439 B2 | 4/2016 | Iwamoto et al. | |
| 9,492,431 B2 | 11/2016 | Kimura | |
| 9,750,721 B2 | 9/2017 | Kimura | |
| 2002/0082265 A1 | 6/2002 | Lapierre et al. | |
| 2003/0113913 A1 | 6/2003 | Purton et al. | |
| 2003/0114482 A1 | 6/2003 | Pacifici et al. | |
| 2003/0125252 A1 | 7/2003 | Underhill et al. | |
| 2005/0271705 A1 | 12/2005 | Hughes et al. | |
| 2006/0210638 A1* | 9/2006 | Liversidge | A61K 9/0019 424/489 |
| 2009/0074789 A1 | 3/2009 | Sabbadini et al. | |
| 2009/0176862 A1 | 7/2009 | Chandraratna et al. | |
| 2009/0214493 A1 | 8/2009 | Pittenger et al. | |
| 2009/0281184 A1 | 11/2009 | Sawada et al. | |
| 2011/0076318 A1 | 3/2011 | Hughes et al. | |
| 2012/0077786 A1 | 3/2012 | Byron et al. | |
| 2013/0189319 A1 | 7/2013 | Cook et al. | |
| 2014/0303223 A1 | 10/2014 | Iwamoto et al. | |
| 2014/0363402 A1 | 12/2014 | Iwamoto et al. | |

(Continued)

FOREIGN PATENT DOCUMENTS

| | | |
|---|---|---|
| CN | 1468207 A | 1/2004 |
| EP | 0747347 A1 | 12/1996 |

(Continued)

OTHER PUBLICATIONS

Stolk et. al. (Eur. Respir. J. (2012) 40:306-312).*
Extended European Search Report for European Application No. 13854101.6, dated Apr. 19, 2016 (8 pages).
Bergman et al., "Two improved and simplified methods for the spectrophotometric determination of hydroxyproline," Anal. Chem. 35(12):1961-5 (1963).
Danziger et al., "Automated site-directed drug design: a general algorithm for knowledge acquisition about hydrogen-bonding regions at protein surfaces," Proc R Soc Lond B Biol Sci. 236(1283):101-13 (1989).
Di Rocco et al., "Selective RARγ agonist blocks heterotopic ossification and promotes skeletal muscle repair," ASBMR Oct. 4, 2013, (Abstract only) (2 pages).
Di Rocco et al., "Selective retinoic acid receptor γ agonists promote repair of injured skeletal muscle in mouse," Am J Pathol. 185(9):2495-504 (2015).

(Continued)

*Primary Examiner* — Marcos L Sznaidman
(74) *Attorney, Agent, or Firm* — Clark & Elbing LLP

(57) ABSTRACT

The present invention addresses the problem of providing an inhibitor for retinochoroidal disorders, in particular, an inhibitor for retinochoroidal scar formation and retinochoroidal atrophy in an epiretinal, intraretinal or subretinal tissue. This problem can be solved by preparing an inhibitor for retinochoroidal disorders which comprises, as an active ingredient, (E)-4-(2-{3-[(1H-pyrazol-1-yl)methyl]-5,5,8,8-tetramethyl-5,6,7,8-tetrahydronaphthalene-2-yl}vinyl)benzoic acid, an ester thereof or a salt of the same. The inhibitor for retinochoroidal disorders can inhibit collagen atrophy of retinal pigment epithelium cells, fibroblasts, glial cells and the like and thus inhibit retinochoroidal disorders.

18 Claims, 1 Drawing Sheet

(56) References Cited

U.S. PATENT DOCUMENTS

| | | |
|---|---|---|
| 2015/0290172 A1 | 10/2015 | Kimura |
| 2017/0065562 A1 | 3/2017 | Kimura |

FOREIGN PATENT DOCUMENTS

| | | |
|---|---|---|
| EP | 1938815 A1 | 7/2008 |
| JP | H08-333318 A | 12/1996 |
| JP | H11503998 A | 4/1999 |
| JP | 2004-510728 A | 4/2004 |
| JP | 2005-206544 A | 8/2005 |
| JP | 2007-535563 A | 12/2007 |
| JP | 2009-235031 A | 10/2009 |
| JP | 2013-536855 A | 9/2013 |
| TW | 200538163 A | 12/2005 |
| WO | WO-2001/080894 A2 | 11/2001 |
| WO | WO-2002/028810 A2 | 4/2002 |
| WO | WO-2005/107707 A1 | 11/2005 |
| WO | WO-2007/037188 A1 | 4/2007 |
| WO | WO-2007/113122 A1 | 10/2007 |
| WO | WO-2008/057930 A2 | 5/2008 |
| WO | WO-2010/071583 A1 | 6/2010 |
| WO | WO-2010/088735 A1 | 8/2010 |
| WO | WO-2012/030919 A2 | 3/2012 |
| WO | WO-2012/125724 A1 | 9/2012 |
| WO | WO-2012/129562 A2 | 9/2012 |
| WO | WO-2013/052647 A2 | 4/2013 |
| WO | WO-2014/073209 A1 | 5/2014 |

OTHER PUBLICATIONS

Einhorn et al., "Bone regeneration: new findings and potential clinical applications," J Am Acad Orthop Surg. 9(3):157-65 (2001).
English translation of Japanese Patent Application No. 2005-206544, dated Nov. 23, 2015 (14 pages).
English Translation of Office Action for Eurasian Patent Application No. 201370051, dated Jun. 1, 2015 (4 pages).
Extended European Search Report for European Patent Application No. 11822537.4, dated Feb. 7, 2014 (10 pages).
Halevy et al., "Retinoic acid induces adult muscle cell differentiation mediated by the retinoic acid receptor-α." J Cell Physiol. 154(3):566-72 (1993).
International Search Report and English Translation for International Patent Application No. PCT/2014/002667, dated Aug. 5, 2014 (5 pages).
International Search Report and English Translation for International Patent Application No. PCT/JP2013/006563, dated Dec. 10, 2013 (5 pages).
International Search Report for International Application No. PCT/US2011/049905, dated May 1, 2012 (4 pages).
Iwamoto et al., "Retinoic acid induces rapid mineralization and expression of mineralization-related genes in chondrocytes," Exp Cell Res 207(2): 413-420 (1993).
Japanese Office Action with English translation for Japanese Patent Application No. 2013-527250, dated Jul. 30, 2015 (6 pages).
Jo et al., "Establishment of a new animal model of focal subretinal fibrosis that resembles disciform lesion in advanced age-related macular degeneration," Invest Ophthalmol Vis Sci. 52(9):6089-95 (2011).
Kaplan et al., "Derailing heterotopic ossification and RARing to go," Nat Med. 17(4):420-421 (2011).
Kennedy et al., "Retinoic acid enhances skeletal muscle progenitor formation and bypasses inhibition by bone morphogenetic protein 4 but not dominant negative beta-catenin," BMC Biol. 7:67 (2009). (21 pages).
Koyama et al., "Retinoid signaling is required for chondrocyte maturation and endochondral bone formation during limb skeletogenesis," Dev Biol. 208(2):375-91 (1999).
Krueger C et al., "Identification of Retinoic Acid in a High Content Screen for Agents that Overcome the Anti-Myogenic Effect of TGF-Beta-1," PLoS ONE 5(11): e15511 (2010) (11 pages).

Le May et al., Retinoid X Receptor Signalling in the Specification of Skeletal Muscle Lineage. *Skeletal Muscle—From Myogenesis to Clinical Relations*. Juliana Cseri, 49-72 (2012).
Nagano et al., "Stimulatory effect of pseudomonal elastase on collagen degradation by cultured keratocytes," Invest Ophthalmol Vis Sci. 42(6):1247-53 (2001).
Neuville et al., "Retinoic acid regulates arterial smooth muscle cell proliferation and phenotypic features in vivo and in vitro through an RARα-dependent signaling pathway." Arterioscler Thromb Vasc Biol. 19:1430-6 (1999).
Office Action and its English translation for Chinese Patent Application No. 201180052926.X, dated May 8, 2014 (19 pages).
Office Action for U.S. Appl. No. 14/308,570, dated Jul. 31, 2014 (7 pages).
Pacifici et al., "Vitamin a inhibits chondrogenesis but not myogenesis," Exp Cell Res. 129(2):469-74 (1980) (Abstract Only).
Pacifici et al., Annual Report for U.S. Army Medical Research and Material Command, Oct. 2014, "Preventative Therapeutics for Heterotopic Ossification," (13 pages).
Pakala et al., "RAR gamma agonists inhibit proliferation of vascular smooth muscle cells," J Cardiovasc Pharmacol. 35(2):302-8 (2000).
Patent Examination Report No. 1 for New Zealand Patent Application No. 607547, dated Oct. 21, 2013 (3 pages).
Patent Examination Report No. 1 in Australian Patent Application No. 2011296080, dated Jul. 4, 2014 (4 pages).
Rochette-Egly et al., "Dynamic and combinatorial control of gene expression by nuclear retinoic acid receptors (RARs)," Nuclear Receptor Signaling. 7:1-18 (2009).
Schneider et al., "Activation of retinoic acid receptor alpha is sufficient for full induction of retinoid responses in SK-BR-3 and T47D human breast cancer cells," Cancer Res. 60(19):5479-87 (2000).
Seale et al., "The potential of muscle stem cells," Dev Cell. 1(3):333-42 (2001).
Shimono et al., "A retinoid composition for rapid muscle repair and regeneration." Poster presented at BioTech 2010 Conference (Oct. 27, 2010).
Shimono et al., "Inhibition of ectopic bone formation by a selective retinoic acid receptor alpha-agonist: A new therapy for heterotopic ossification?," J Orthop Res. 28(2): 271-277 (2010).
Shimono et al., "Potent inhibition of heterotopic ossification by nuclear retinoic acid receptor-γ agonists," Nat Med. 17(4):454-60 (2011).
Soprano et al., "Role of retinoic acid in the differentiation of embryonal carcinoma and embryonic stem cells." Vitam horm. 75:69-95 (2007).
Sun et al.,"The synthetic retinoid CD437 selectively induces apoptosis in human lung cancer cells while sparing normal human lung epithelial cells," Cancer Res. 62(8):2430-6 (2002).
Thacher et al., "Therapeutic applications for ligands of retinoid receptors," Curr Pharm Des. 6(1):25-58 (2000).
Weston et al., "Requirement for RAR-mediated gene repression in skeletal progenitor differentiation," J Cell Biol. 158(1):39-51 (2002).
Weston et al., "Revisiting the role of retinoid signaling in skeletal development," Birth Defects Res C Embryo Today. 69(2):156-73 (2003).
Williams et al., "Retinoic acid receptors are required for skeletal growth, matrix homeostasis and growth plate function in postnatal mouse," Dev Biol. 328(2):315-27 (2009).
Yasuhara et al. "Wnt/beta-catenin and retinoic acid receptor signaling pathways interact to regulate chondrocyte function and matrix turnover." J Biol Chem. 285(1):317-327 (2010).
Zasloff et al., "Treatment of patients who have fibrodysplasia ossificans progressiva with isotretinoin," Clin Orthop Relat Res. 346:121-9 (1998).
International Preliminary Report on Patentability for International Application No. PCT/JP2014/002667, dated Dec. 1, 2014 (10 pages).
Gayton, "Etiology, prevalence, and treatment of dry eye disease," Clin Ophthalmol. 3:405-12 (2009).
Javadi et al., "Dry eye syndrome," J Ophthalmic Vis Res. 6(3):192-8 (2011).

(56) References Cited

OTHER PUBLICATIONS

Kim et al., "A comparison of vitamin a and cyclosporine a 0.05% eye drops for treatment of dry eye syndrome," Am J Ophthalmol. 147(2):206-13e2 (2009).
Lemp, "Management of dry eye disease," Am J Manag Care. 14(3 Suppl):S88-101 (2008).
Nezzar et al., "Molecular and metabolic retinoid pathways in the human ocular surface," Mol Vis. 13:1641-50 (2007).
Samarawickrama et al., "Retinoic acid and the ocular surface," Surv Ophthalmol. 60(3):183-95 (2015).
Junko et al., "38. Efficacy of retinoic acid receptor-specific agonist on choroidal neovascularization in mice," Research on Retinochoroidal and Optic Atrophy Heisei 15 Nendo Sokatsu 209-11 (2004).
Tseng et al., "Topical retinoid treatment for various dry-eye disorders," Ophthalmology 92(6):717-27 (1985).
Acera et al., "Inflammatory Markers in the Tears of Patients with Ocular Surface Disease," Ophthalmic Res. 40(6):315-321 (2008).
Baudouin, "Un nouveau schema pour mieux comprendre les maladies de la surface oculaire," J Fr. Ophthalmol. 30(3):239-246 (2007) (English abstract included).
Bose et al., "Dry eye disease and uveitis: A closer look at immune mechanisms in animal models of two ocular autoimmune diseases," Autoimmun Rev. 15(12):1181-1192 (2016).
Chotikavanich et al., "Production and Activity of Matrix Metalloproteinase-9 on the Ocular Surface Increase in Dysfunctional Tear Syndrome," available in PMC Mar. 12, 2013, published in final edited form as: Invest Ophthalmol Vis Sci. 50(7):3203-3209 (2009) (18 pages).
Corrales et al., "Desiccating Stress Stimulates Expression of Matrix Metalloproteinases by the Corneal Epithelium," Invest Ophthalmol Vis Sci.47(8):3293-3302 (2006).
De Paiva et al., "Corticosteroid and doxycycline suppress MMP-9 and inflammatory cytokine expression, MAPK activation in the corneal epithelium in experimental dry eye," Exp Eye Res. 83(3):526-535 (2006).
De Paiva et al., "Disruption of TGF-beta Signaling Improves Ocular Surface Epithelial Disease in Experimental Autoimmune Keratoconjunctivitis Sicca," PLoS ONE. 6(12):e29017 (2011) (9 pages).
Editors: Foulks et al. "2007 Report of the International Dry Eye Workshop (DEWS)," The Ocular Surface. 5(2):65-67; 69-193; 195-199; 202 (2007) (138 pages).
Huet et al., "EMMPRIN Modulates Epithelial Barrier Function through a MMP-Mediated Occludin Cleavage: Implications in Dry Eye Disease," Am J Pathol. 179(3):1278-1286 (2011).
Lee et al., "Minocycline Controls Clinical Outcomes and Inflammatory Cytokines in Moderate and Severe Meibomian Gland Dysfunction," Am J Ophthalmol. 154(6):949-957 (2012).
Luo et al., "Experimental Dry Eye Stimulates Production of Inflammatory Cytokines and MMP-9 and Activates MAPK Signaling Pathways on the Ocular Surface," Invest Ophthalmol Vis Sci. 45(12):4293-4301 (2004).
Mori et al., "A Highly Soluble Matrix Metalloproteinase-9 Inhibitor for Potential Treatment of Dry Eye Syndrome," Basic Clin Pharmacol Toxicol. 111(5):289-295 (2012).
Pflugfelder et al., "Matrix Metalloproteinase-9 Knockout Confers Resistance to Corneal Epithelial Barrier Disruption in Experimental Dry Eye," Am J Pathol. 166(1):61-71 (2005).
Reichel et al., "New model of conjunctival scarring in the mouse eye," Br J Ophthalmol. 82(9):1072-1077 (1998).
Sakimoto et al., "Metalloproteinases in Corneal Diseases: Degradation and Processing," Cornea. 31 Suppl 1(11):S50-6 (2012).
Smith et al., "Tear film MMP accumulation and corneal disease," Br J Ophthalmol. 85(2):147-153 (2001).
Solomon et al., "Pro- and Anti-inflammatory Forms of Interleukin-1 in the Tear Fluid and Conjunctiva of Patients with Dry-Eye Disease," Invest Ophthalmol Vis Sci. 42(10):2283-2292 (2001).
Stern et al., "A unified theory of the role of the ocular surface in dry eye," Adv Exp Med Biol. 438:643-651 (1998).
Stern et al., "Autoimmunity at the ocular surface: pathogenesis and regulation," Mucosal Immunol. 3(5):425-442 (2010).
Stevenson et al., "Dry eye disease: an immune-mediated ocular surface disorder," available in PMC Jun. 10, 2013, published in final edited form as: Arch Ophthalmol. 130(1):90-100 (2012) (19 pages).
Kimura et al., "Suppression by an RAR-gamma Agonist of Collagen Degradation Mediated by Corneal Fibroblasts," Invest Ophthalmol Vis Sci. 58(4):2250-2257 (2017).
Hind et al., "Is a regenerative approach viable for the treatment of COPD?" Br J Pharmacol. 163(1):106-115 (2011).
Jones et al., "Tesra (treatment of Emphysema with a selective retinoid agonist) study results," C91 Late Breaking Clinical Trials Symposium, May 17, Denver, CO. Am J Respir Crit Care Med. 183:A6418 (2011).
Wozney et al., "Novel regulators of bone formation: molecular clones and activities," Science. 242(4885):1528-34 (1988).
Duncan et al., "The link between heparan sulfate and hereditary bone disease: finding a function for the EXT family of putative tumor suppressor proteins," J Clin Invest. 108(4):511-6 (2001).
Matsumoto et al., "Conditional ablation of the heparan sulfate-synthesizing enzyme Ext1 leads to dysregulation of bone morphogenic protein signaling and severe skeletal defects," J Biol Chem. 285(25):19227-34 (2010).
Extended European Search Report for European Application No. 18183955.6, dated Jan. 3, 2019 (9 pages).
Communication pursuant to Article 94(3) EPC for European Patent Application No. 13854101.6, dated Jul. 26, 2018 (6 pages).
First Examination Report for New Zealand Patent Application No. 708756, dated Sep. 25, 2018 (3 pages).
Caffery et al., "Ocular side effects of isotretinoin therapy," J Am Optom Assoc. 59(3):221-4 (1988) (Abstract Only).
Du et al., "Retinoic acid suppresses the adhesion and migration of human retinal pigment epithelial cells," Exp Eye Res. 109:22-30 (2013).
Lebowitz et al., "Ocular effects of oral retinoids," J Am Acad Dermatol. 19(1 Pt 2):209-11 (1988).
Safran et al., Ocular Side Effects of Oral Treatment with Retinoids: A Review of Clinical Findings and Molecular Mechanisms, and a Prospective Study of the Influence of Acitretin on Retinal Function. Retinoids: 10 Years on. Saurat J-H, 315-326 (1991).
Yan et al., "Antiproliferative effect of sustained drug delivery system of all-trans retinoic acid implant into rabbit's vitreous cavity for treatment of proliferative vitreoretinopathy," Zhonghua Yan Ke Za Zhi. 39(10):621-5 (2003) (Abstract Only).
Yasunari et al., "Effect of Retinoic Acid on Proliferation and Polyamine Metabolism in Cultured Bovine Retinal Pigment Epithelial Cells," Ophthalmic Res. 31(1):24-32 (1999).
Liu et al., "All-trans-retinoic acid inhibition of transforming growth factor-β-induced collagen gel contraction mediated by human Tenon fibroblasts: role of matrix metalloproteinases," Br J Ophthalmol. 99(4):561-65 (2015).
Rhee, Sangmyung. "Fibroblasts in three dimensional matrices: cell migration and matrix remodeling," Exp Mol Med. 41(12):858-65 (2009).
Agadir et al., "Retinyl Methyl Ether Down-Regulates Activator Protein 1 Transcriptional Activation in Breast Cancer Cells," Cancer Research. 57(6):3444-50 (1997).
Araiz et al., "Antiproliferative Effect of Retinoic Acid in Intravitreous Silicone Oil in an Animal Model of Proliferative Vitreoretinopathy," Inv Ophthalmol & Vis Sci. 34(3):522-30 (1993).
Benkoussa et al., "Retinoic Acid Receptors Inhibit AP1 Activation by Regulating Extracellular Signal-Regulated Kinase and CBP Recruitment to an AP1-Responsive Promoter," Mol Cell Biol. 22(13):4522-34 (2002).
Campochiaro, "Pathogenic Mechanisms in Proliferative Vitreoretinopathy," Arch Ophthalmol. 115(2):237-41 (1997).
Chen et al., "Transcriptional Regulation by Transforming Growth Factor β of the Expression of Retinoic Acid and Retinoid X Receptor Genes in Osteoblastic Cells is Mediated through AP-1," Journ Biol Chem. 271(49):31602-6 (1996).
Dedieu et al., "Retinoids interfere with the AP1 signalling pathway in human breast cancer cells," Cell Signal. 18(6):889-98 (2006).

(56) References Cited

OTHER PUBLICATIONS

Giordano et al., "Sustained delivery of Retinoic Acid from Microspheres of Biodegradable Polymer in PVR," Inv Ophthalmol & Vis Sci. 34(9):2743-51 (1993).
Hu et al., "A novel retinoic acid analog, 4-amino-2-trifluoromethyl-phenyl retinate, inhibits gastric cancer cell growth," Int Journ Mol Med. 33(2):415-22 (2014).
Huang et al., "Retinoic Acid Actions Through Mammalian Nuclear Receptors," available in PMC on Jan. 8, 2015, published in final edited form as: Chem Rev. 114(1):233-54 (2014).
Kirchmeyer et al., "All-trans retinoic acid suppresses interleukin-6 expression in interleukin-1stimulated synovial fibroblasts by inhibition of ERK pathway independently of RAR activation," Arthritis Research. 10(6):R141 (2008) (12 pages).
Lefebvre et al., "Transcriptional Activities of Retinoic Acid Receptors," Vitamins and Hormones. 70:199-264 (2005).
Nagpal et al., "Separation of Transactivation and AP1 Antagonism Functions of Retinoic Acid Receptor α*," Journ Bio Chem. 270(2):923-27 (1995).
Pfahl, "Nuclear Receptor/Ap-1 Interaction*," Endocrine Reviews. 14(5):651-8 (1993).
Schadendorf et al., "Treatment of Melanoma Cells with the Synthetic Retinoid CD437 Induces Apoptosis via Activation of Ap-1 in Vitro, and Causes Growth Inhibition in Xenografts in Vivo," Journ Cell Biol. 135(6):1889-98 (1996).
Stolk et al., "Randomised controlled trial for emphysema with a selective agonist of the γ-type retinoic acid receptor," Eur Respir J. 40(2):306-12 (2012).
Sun et al., "Induction of Apoptosis in Human Non-Small Cell Lung Carcinoma Cells by the Novel Synthetic Retinoid CD437," J Cell Phys. 173(2):279-284 (1997).
Tsai et al., "Extracellular Signals Regulate Rapid Coactivator Recruitment at Ap-1 Sites by Altered Phosphorylation of both CREB Binding Protein and c-jun," Mol Cell Biol. 28(13):4240-50 (2008).
Vincenti et al., "v-src Activation of the Collagenase-1 (Matrix Metalloproteinase-1) Promoter through PEA3 and STAT: Requirement of Extracellular Signal-Regulated Kinases and Inhibition by Retinoic Acid Receptors," Mol Carc. 21(3):194-204 (1998).
Widschwendter et al., "Activity of Retinoic Acid Receptor-γ Selectively Binding Retinoids Alone and in Combination with Interferon-γ in Breast Cancer Cell Lines," Int J Cancer. 71(3):497-504 (1997).
Stolk et al., "Retinoid treatment of Emphysema in Patients on the Alpha-1 International Registry. The REPAIR study: study design, methodology and quality control of study assessments," Ther Adv Respir Dis. 4(6):319-32 (2010).
Chang et al., "Effect of Oral 13-Cis-Retinoic Acid Treatment on Postoperative Clinical Outcome of Eyes With Proliferative Vitreoretinopathy," Am Journ Ophthalmol. 146(3):440-6 (2008).
Fekrat et al., "The Effect of Oral 13-cis-retinoic Acid on Retinal Redetachment after Surgical Repair in Eyes with Proliferative Vitreoretinopathy," Ophthalmol. 102(3):412-18 (1995).
Gollapalli et al., "The specific binding of retinoic acid to RPE65 and approaches to the treatment of macular degeneration," Proc Nat Acad Sci. 101(27):10030-5 (2004).
Veloso Jr. et al., "13-cis-Retinoic Acid in Silicone-Fluorosilicone Copolymer Oil in a Rabbit Model of Proliferative Vitreoretinopathy," Exp Eye Res. 65(3):425-34 (1997).
Wu et al., "Effects of Retinoic Acid on Retinal Pigment Epithelium from Excised Membranes from Proliferative Vitreretinopathy," Journ Ocul Pharm Ther. 21(1):44-54 (2004).
Klaassen et al., "Metabolism and growth inhibition of four retinoids in head and neck squamous normal and malignant cells," Brit Journ Canc. 85(4):630-35 (2001).
Fanjul et al., "A new class of retinoids with selective inhibition of Ap-1 inhibits proliferation," Nature. 372(6501):107-11 (1994).

\* cited by examiner

| Benzoic acid of the invention (μM) | 0 | 0 | 0.01 | 0.1 | 1 |
| TGF-β2 (ng/ml) | 0 | 1 | 1 | 1 | 1 |

INHIBITOR FOR RETINOCHOROIDAL DISORDERS

The present invention relates to an inhibitor of retinochoroidal disorder comprising (E)-4-(2-{3-[(1H-pyrazol-1-yl)methyl]-5,5,8,8-tetramethyl-5,6,7,8-tetrahydronaphthalene-2-yl}vinyl)benzoic acid, an ester thereof or a salt thereof as an effective ingredient.

BACKGROUND ART

In Japan where the society has an aging population, the ratio of vitreoretinal diseases such as diabetic retinopathy, retinal detachment, and age-related macular degeneration is expected to continue to increase as a cause of blindness. Prognosis of such diseases, which resulted in blindness in the past, is improving by the development of vitreoretinal operation and introduction of biopharmaceuticals, such as anti-VERF intraocular injections. However, aside from initial symptoms, the prognosis of visual functions in severe cases, where symptoms were left untreated for a long period of time or are recurring, is still not favorable. Even if retinopexy is attained by an operation or intraocular neovascularity can be devised to disappear with a pharmaceutical agent, photoreceptor functions would decrease if retinal cells have already suffered an irreversible secondary damage. Eyes are organs, for which healing of injury would be completely meaningless if photoreceptor functions are lost. Thus, in order to maintain normal retinal functions, it is important how an ophthalmic inflammation and the following secondary reaction can be controlled with the least amount of damage.

Along with the calming or progression of an ophthalmic inflammation, a retinochoroidal fibrotic scar is often formed in epiretinal, intraretinal, or subretinal tissue and in some cases leads to a disorder in photoreceptor cell functions. Collagen, which is one of the components of the stroma and retinal pigment epithelial cells, particularly type I collagen, is known as a representative cell component constituting a retinochoroidal fibrotic scar. Retinochoroidal dysfunction occurs due to the formation and atrophy of a retinochoroidal fibrotic scar. In this regard, it is considered effective against retinochoroidal disorders to inhibit atrophy of collagen, particularly type I collagen, of retinal pigment epithelial cells or the like to prevent deformation or disintegration of a tissue structure.

To date, a medicament for the prevention and/or treatment of diabetic retinopathy or age-related macular degeneration having an agonist of a retinoic acid receptor (hereinafter, also referred to as "RAR"), all-trans retinoic acid or 4-[(5,6,7,8-tetrahydro-5,5,8,8-tetramethyl-2-naphthalenyl)carbamoyl]benzoic acid, as an effective ingredient (for example, see Patent Literature 1). However, since such an effective ingredient does not have selectivity with respect to RAR subtypes RARα and RARβ, the contribution of each RAR subtype to improvement in the retinal function is unknown. Meanwhile, RAR is involved in various effects such as growth, morphogenesis, and differentiation in many cells such as inflammatory cells, immune cells, and structural cells. Further, it is verified that there is a difference in the distribution of RAR subtypes depending on the tissue or organ of a mammal. Some of the effects of RAR are undesirable, such as increase in triglyceride due to RARα. Thus, the specificity or selectivity with respect to subtypes in compounds with RAR agonist activity is expected to lead to reduction in risk of side effects. For the above reasons, there is a demand for RAR agonists, which have a strong effect of inhibiting retinochoroidal disorders and are highly safe based on subtype selectivity.

(E)-4-(2-{3-[(1H-pyrazole-1-yl)methyl]-5,5,8,8-tetramethyl-5,6,7,8-tetrahydronaphthalene-2-yl}vinyl)benzoic acid is disclosed to be useful as a RARγ selective agonist against pulmonary emphysema, cancer, and dermatosis (for example, see Patent Literature 2) and against neurological pain (for example, see Patent Literature 3). However, there is no study that has examined the pharmacological effect of (E)-4-(2-{3-[(1H-pyrazole-1-yl)methyl]-5,5,8,8-tetramethyl-5,6,7,8-tetrahydronaphthalene-2-yl}vinyl)benzoic acid, an ester thereof, or a salt thereof on retinochoroidal disorders, particularly the formation and atrophy of a retinochoroidal scar, or a document suggesting such an effect.

[PTL 1] Domestic Publication of PCT International Publication No. 2007/037188
[PTL 2] International Publication No. WO 2002/028810 pamphlet
[PTL 3] International Publication No. WO 2008/057930 pamphlet

SUMMARY OF INVENTION

The objective of the present invention is to provide an inhibitor for a retinochoroidal disorder, particularly an inhibitor for the formation and atrophy of a retinochoroidal scar in epiretinal, intraretinal, or subretinal tissue.

The search for a drug that is effective against ophthalmic diseases, particularly retinochoroidal disorders in vitreoretinal diseases, is an objective that is important and of interest in the field of ophthalmology. After diligent research to find a drug that is effective in inhibiting retinochoroidal disorders, particularly the formation and atrophy of a retinochoroidal scar, the inventors discovered that the RARγ selective agonist (E)-4-(2-{3-[(1H-pyrazole-1-yl)methyl]-5,5,8,8-tetramethyl-5,6,7,8-tetrahydronaphthalene-2-yl}vinyl)benzoic acid exerts an excellent effect of amelioration in inhibiting the formation and atrophy of a retinochoroidal scar by pharmacological tests using murine retinal pigment epithelial cells, wherein the above-described benzoic acid exhibited an effect of inhibiting collagen atrophy and an effect of inhibiting the formation and atrophy of subretinal scars in mice to complete the present invention.

Specifically, the present invention is directed to [1] an inhibitor for a retinochoroidal disorder comprising (E)-4-(2-{3-[(1H-pyrazole-1-yl)methyl]-5,5,8,8-tetramethyl-5,6,7,8-tetrahydronaphthalene-2-yl}vinyl)benzoic acid, an ester thereof, or a salt thereof as an effective ingredient, [2] the inhibitor for a retinochoroidal disorder of the above-described [1], wherein the (E)-4-(2-{3-[(1H-pyrazole-1-yl)methyl]-5,5,8,8-tetramethyl-5,6,7,8-tetrahydronaphthalene-2-yl}vinyl)benzoic acid, the ester thereof, or the salt thereof is (E)-4-(2-{3-[(1H-pyrazole-1-yl)methyl]-5,5,8,8-tetramethyl-5,6,7,8-tetrahydronaphthalene-2-yl}vinyl)benzoic acid or a salt thereof, [3] the inhibitor for a retinochoroidal disorder of the above-described [1] or [2], wherein the retinochoroidal disorder is formation or atrophy of a retinochoroidal scar in epiretinal, intraretinal, or subretinal tissue, [4] the inhibitor for a retinochoroidal disorder according to any one of the above-described [1]-[3], wherein a form of administration is instillative administration or oral administration, and [5] the inhibitor for a retinochoroidal disorder accordingly to any one of the above-described [1]-[4], wherein a dosage form is an instillation, an ophthalmic ointment, an injection, a tablet, a granule, a fine granule, a powder or a capsule.

(E)-4-(2-{3-[(1H-pyrazole-1-yl)methyl]-5,5,8,8-tetramethyl-5,6,7,8-tetrahydronaphthalene-2-yl}vinyl)benzoic acid, an ester thereof, or a salt thereof, which is an effective ingredient of the inhibitor for a retinochoroidal disorder of the present invention, is useful as an inhibitor for retinochoroidal disorders, particularly as an inhibitor for the formation and atrophy of a retinochoroidal scar, by inhibiting collagen atrophy of a retinal pigment epithelial cell, fibroblast, glial cell or the like.

BRIEF DESCRIPTION OF DRAWINGS

FIG. 2A shows the results of subretinal observation after 7 days from the injection of 50 μg of the benzoic acid of the present invention and macrophages. FIG. 2B shows the results of measuring a subretinal scar region after 7 days from injection when injecting 1 μg, 5 μg, or 50 μg of the benzoic acid of the invention and macrophages, wherein '*' indicates the presence of a statistically significant difference (p<0.05).

DESCRIPTION OF EMBODIMENTS

Figure 1:
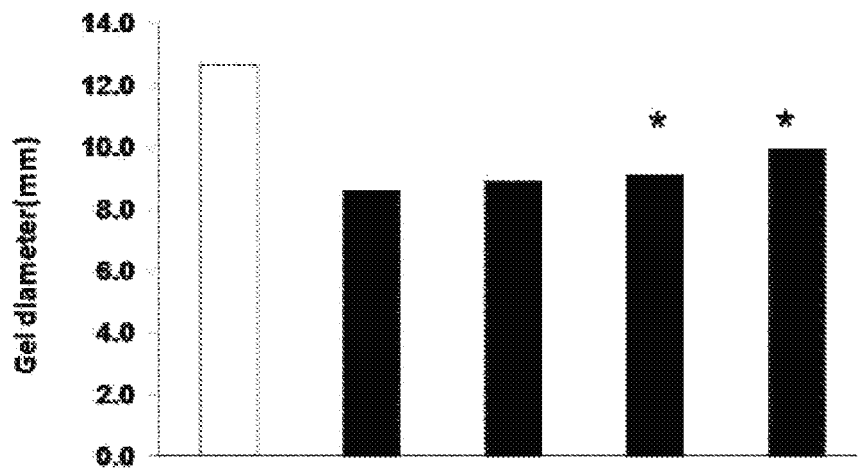
FIG. 1 is a graph showing the relationship between the concentration (μM) of (E)-4-(2-{3-[(1H-pyrazole-1-yl)methyl]-5,5,8,8-tetramethyl-5,6,7,8-tetrahydronaphthalene-2-yl}vinyl)benzoic acid (hereinafter, also referred to as "benzoic acid of the invention") and collagen atrophy (diameter (mm) of collagen gel in the dish) when using murine retinal pigment epithelial cells, wherein '*' indicates the presence of a statistically significant difference (p<0.05).

The inhibitor for a retinochoroidal disorder of the present invention is not particularly limited and may be any inhibitor having the benzoic acid of the invention represented by the following formula (I), an ester thereof, or a salt thereof as the effective ingredient. However, the benzoic acid of the invention or a salt thereof is preferable as an effective ingredient. Further, other embodiments of the present invention include: a method of treating a retinochoroidal disorder characterized in administering the benzoic acid of the invention, an ester thereof, or a salt thereof to a subject; the benzoic acid of the invention, an ester thereof, or a salt thereof for use as an inhibitor for a retinochoroidal disorder; and use of the benzoic acid of the invention, an ester thereof, or a salt thereof in the preparation of an inhibitor for a retinochoroidal disorder.

[Chemical 1]

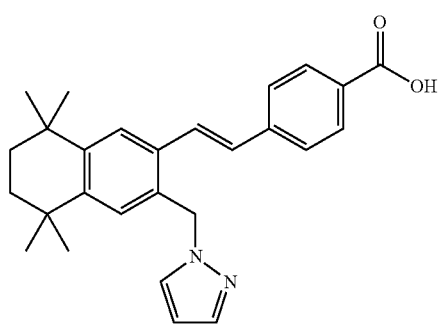

(I)

In the present invention, a retinochoroidal disorder refers to a condition in which an injury occurs to a photoreceptor cell, ganglion cell, retinal pigment epithelial cell or tissue comprised of each of the above-described cells in the retina or choroid, ultimately leading to cell death or tissue dysfunction to cause disturbance in visual function such as vision or field of vision. A retinochoroidal disorder is suitably exemplified by formation and atrophy of a retinochoroidal scar and vitreoretinal diseases such as diabetic retinopathy, age-related macular degeneration, retinal detachment, proliferative vitreoretinopathy, uveitis, ocular infection, retinopathy of prematurity, neovascular maculopathy, and retinochoroiditis. A retinochoroidal disorder is particularly suitably exemplified by formation and atrophy of a retinochoroidal scar.

In the present invention, a retinochoroidal scar is a fibrous connective tissue occurring at an epiretinal, intraretinal, or subretinal injury site with the soothing or progression of an ophthalmic inflammation, preferably a fibrous connective tissue occurring at a subretinal injury site, and is mainly tissue comprised of a retinal pigment epithelial cell, fibroblast, glial cell, or the like with extracellular matrix including collagen. In addition, the above-described epiretinal refers to on a retinal surface, subretinal refers to between the retina and choroid, inside the choroid, and under the choroid. Further, formation of a retinochoroidal scar refers to the formation of a fibrous connective tissue at an epiretinal, intraretinal, or subretinal injury site with the soothing or progression of an ophthalmic inflammation. Atrophy of a retinochoroidal scar refers to the atrophy by a formed retinochoroidal scar pulling tissue in the periphery thereof upon healing. Such formation and atrophy of a retinochoroidal scar occurs in series. It is possible to prevent peripheral tissue and macular area of a retinochoroidal scar from deforming to cause a disorder in the retinochoroidal function by inhibiting the formation and atrophy of the retinochoroidal scar.

The benzoic acid of the invention, an ester thereof, or a salt thereof, which is an effective ingredient of the therapeutic agent for a retinochoroidal disorder of the present invention, can be manufactured in accordance with the method described in Patent Literature 2 described above or purchased as a commercially-available product. Examples of such commercially-available products include product name: palovarotene manufactured by Shanghai Haoyuan Chemexpress.

Esters in the benzoic acid of the invention, an ester thereof, or a salt thereof, which is an effective ingredient of the therapeutic agent for a retinochoroidal disorder of the present invention, are not particularly limited and can be any ester converted to the benzoic acid of the invention in a reaction by an enzyme or the like under physiological conditions in vivo. Examples of such esters include: esters generated by reaction with a primary alcohol, such as methanol, ethanol, propanol, hexanol, dodecanal or the like; esters generated by reaction with a secondary alcohol such as isopropanol, s-butanol, 1-ethylpropanol or the like; esters generated by reaction with a tertiary alcohol such as t-butanol, 1-methyl-1-ethylpropanol or the like; and esters generated by reaction with an amino alcohol such as 2-aminoethanol or the like.

The above-described esters can be manufactured by a known method from the benzoic acid of the invention or an intermediate during synthesis thereof.

Salts in the benzoic acid of the invention, an ester thereof, or a salt thereof, which is an effective ingredient of the inhibitor for a retinochoroidal disorder of the present invention, are not particularly limited and can be any pharmaceutically acceptable salts. Such salts include (1) as an acid addition salt, inorganic acid salts such as hydrochloride, hydrobromic acid salt, hydroiodic acid salt, nitric acid salt, sulfuric acid salt, phosphoric acid salt and the like; and organic acid salts such as acetic acid salt, trifluoroacetic acid salt, benzoic acid salt, oxalic acid salt, malonic acid salt, succinic acid salt, maleic acid salt, fumaric acid salt, tartaric acid salt, citric acid salt, methanesulfonic acid salt, ethanesulfonic acid salt, trifluoromethanesulfonic acid salt, benzenesulfonic acid salt, p-toluenesulfonic acid salt, glutamic acid salt, aspartic acid salt and the like and (2) as a basic salt, metal salts such as sodium salt, potassium salt, calcium salt, magnesium salt and the like; inorganic salts such as ammonium salt and the like; and organic amine salts such as triethylamine salt, guanidine salt and the like.

The inhibitor for a retinochoroidal disorder of the present invention can be administered orally or parenterally (intravenous administration, intramuscular administration, intraperitoneal administration, percutaneous administration, intratracheal administration, intracutaneous administration, or subcutaneous administration) in a form of an ointment (preferably ophthalmic ointment), injection, tablet, granule, fine granule, powder, capsule, inhalant, syrup, pill, liquid formulation, suspension, emulsion, percutaneous absorption agent, suppository, or lotion manufactured by mixing in a suitable pharmacologically acceptable additive. These formulations are manufactured by a well-known method by using an additive such as an excipient, lubricant, binding agent, disintegrator, emulsifier, stabilizer, flavoring agent or diluent.

Examples of excipients include organic excipients and inorganic excipients. Examples of organic excipients include: sugar derivatives such as lactose, sucrose, glucose, mannitol, sorbitol and the like; starch derivatives such as corn starch, potato starch, α-starch, dextrin and the like; cellulose derivatives such as crystalline cellulose and the like; gum arabic; dextran; pullulan and the like. Examples of inorganic excipients include: light anhydrous silicic acid; and sulfuric acid salts such as calcium sulfate and the like.

Examples of lubricants include: stearic acid; metal salts of stearic acid such as calcium stearate, magnesium stearate and the like; talc; colloidal silica; wax such as beeswax, spermaceti and the like; boric acid; adipic acid; sulfuric acid salts such as sodium sulfate and the like; glycol; fumaric acid; sodium benzoate; D,L-Leucine, sodium lauryl sulfate; silicic acids such as silica and silicic acid hydrate; and the starch derivatives and the like for the above-described excipients.

Examples of binding agents include hydroxypropyl cellulose, hydroxypropyl methylcellulose, polyvinylpyrrolidone, macrogol and the compounds described above shown for excipients.

Examples of disintegrators include: cellulose derivatives such as hydroxypropyl cellulose with a low degree of substitutions, carboxymethyl cellulose, calcium carboxymethyl cellulose, and internally crosslinked calcium carboxymethyl cellulose and the like; crosslinked polyvinylpyrrolidone; and chemically modified starch or cellulose derivatives or the like such as carboxymethyl starch and sodium carboxymethyl starch and the like.

Examples of emulsifiers include: colloidal clay such as bentonite and veegum and the like; anionic surfactants such as sodium lauryl sulfate and the like; cationic surfactants such as benzalkonium chloride and the like; and non-ionic surfactants and the like such as polyoxyethylene alkyl ether, polyoxyethylene sorbitan fatty acid ester, and sucrose fatty acid ester and the like.

Examples of stabilizers include: para-hydroxybenzoic acid esters such as methylparaben, propylparaben and the like; alcohols such as chlorobutanol, benzyl alcohol, and phenylethyl alcohol and the like; benzalkonium chloride; phenols such as phenol and cresol and the like; thimerosal; acetic anhydride; and sorbic acid.

Examples of flavoring agents include: sweeteners such as sodium saccharin and aspartame and the like; acidulants such as citric acid, malic acid, and tartaric acid and the like; and flavors such as menthol, lemon extract and orange extract and the like.

Diluents are generally compounds used as a diluent. Examples thereof include lactose, mannitol, glucose, sucrose, calcium sulfate, hydroxypropyl cellulose, microcrystalline cellulose, water, ethanol, polyethylene glycol, propylene glycol, glycerol, starch, polyvinylpyrrolidone, mixtures thereof and the like.

For ointments (preferably ophthalmic ointments), a commonly-used base such as white petrolatum or liquid paraffin or the like can be used for preparation.

The inhibitor for a retinochoroidal disorder of the present invention includes those in a form of instillation in addition to the above-described dosage forms. The above-described instillation can be instillatively administered. The agent can be formulated with a well-known method by suitably blending in an isotonizing agent, buffer, pH regulator, solubilizer, thickener, stabilizer, preservative (antiseptic) or the like as an additive. Further, it is also possible to obtain a stable instillation by adding a pH regulator, thickener, dispersant or the like to prepare suspension of a drug.

Examples of isotonizing agents include glycerin, propylene glycol, sodium chloride, potassium chloride, sorbitol, mannitol and the like.

Examples of buffers include phosphoric acid, phosphate, citric acid, acetic acid, ε-aminocaproic acid and the like.

Examples of pH regulators include hydrochloric acid, citric acid, phosphoric acid, acetic acid, sodium hydroxide, potassium hydroxide, boric acid, borax, disodium hydrogen phosphate, sodium dihydrogen phosphate, sodium carbonate, sodium bicarbonate and the like.

Examples of solubilizers include polysorbate 80, polyoxyethylene hydrogenated castor oil 60, macrogol 4000 and the like.

Examples of thickeners and dispersants include: cellulose polymers such as hydroxypropyl methylcellulose, hydroxypropyl cellulose and the like; polyvinyl alcohols; polyvinylpyrrolidone and the like. Further, examples of stabilizers include edetic acid, sodium edetate and the like.

Examples of preservatives (antiseptics) include commonly-used sorbic acid, potassium sorbate, benzalkonium chloride, benzethonium chloride, methyl parahydroxybenzoate, propyl parahydroxybenzoate, chlorobutanol and the like. It is also possible to use these preservatives in combination.

An instillation may have any pH within a range acceptable for an ophthalmic formulation, but the pH is desirably set to 4.0-8.5.

The dosage of the inhibitor for a retinochoroidal disorder of the present invention can be appropriately changed in accordance with the dosage form, severity of symptoms of a patient to whom the agent is to be administered, age, weight, judgment of a physician or the like. For oral agents, it is generally possible to administer 0.01-5000 mg, preferably 0.1-2500 mg, and more preferably 0.5-1000 mg per day for an adult in one or several doses. For instillations, it is possible to administer those with an effective ingredient concentration of 0.000001-10% (W/V), preferably 0.00001-3% (W/V), and more preferably 0.0001-1% (W/V), in one or several daily doses. For ophthalmic ointments, it is possible to administer those with an effective ingredient concentration of 0.00001-10% (W/W), preferably 0.0001-3% (W/W), and more preferably 0.001-1% (W/W), in one or several daily doses.

Hereinafter, the present invention is illustrated in further detail while providing Examples (Test Examples and Drug Formulation Examples). However, the scope of the present invention is not limited thereto.

EXAMPLES

Example 1

(Test on Inhibition of Three-Dimensional Collagen Gel Atrophy in Murine Retinal Pigment Epithelial Cell)

Murine retinal pigment epithelial cells were used to assess the inhibition effect of a tested compound on three-dimensional collagen gel atrophy in accordance with the method of Nishida et al (Investigative Ophthalmology & Visual Science 42: 1247-1253 (2001)). A subretinal sheet-like pigment epithelial cell comprising a retinal pigment epithelial cell from a mouse eyeball was collected and grown in primary culture. The cultured cell was detached and collected from a culture slide with 0.05% Trypsin-EDTA. After washing twice in a serum free medium (MEM: product number 11095; Gibco), a serum-free medium was added to make a cell suspension. Type I collagen (3 mg/ml: product number 637-00653; Nitta Gelatin Inc.), 10×MEM, reconstitution buffer (product number 635-00791; Nitta Gelatin Inc.), cell suspension ($1.1 \times 10^7$ cells/ml in MEM), and water were mixed on ice at the volume ratio of 7:1:1:0.2:1.8. A culture dish coated with 1% BSA was inoculated with the mixture (0.5 ml), which was incubated for one hour at 37° C. to make a collagen gel. Then, 0.5 ml each of serum free media, to which 1 ng/ml of TGF-β2 (R&D) and 0, 0.01, 0.1, or 1 µM of the benzoic acid of the invention were added, was added onto collagen gels and incubated at 37° C. The diameter of gels was measured after 24 hours. As a control, 0.5 ml of only a serum-free medium was added and similarly incubated. The results are shown in FIG. 1.
(Results)

It can be seen from FIG. 1 that the benzoic acid of the invention can inhibit collagen atrophy due to TGF when using murine retinal pigment epithelial cells. This demonstrates that the benzoic acid of the invention contributes to collagen turn over and is effective in inhibiting retinochoroidal disorders and has an effect of inhibiting tissue remodeling that occurs after inflammation, hemorrhage, infection, surgery, or injury in an ophthalmic tissue, i.e., retinal tissue fibrillation, retinochoroidal scar formation, and atrophy.

Example 2

(Test on Inhibition of Murine Subretinal Scar Formation)

A murine subretinal scar model was produced to study whether the benzoic acid of the invention has an effect of inhibiting subretinal scar formation. A subretinal scar model in a mouse was produced by the method shown below in accordance with the method of Young-joon et al (Investigative Ophthalmology & Visual Science, 52, 6089-6095 (2001)).

(Production of Murine Subretinal Scar Model)

First, laser was irradiated (0.05 seconds, 200 mW, 532 nm) onto one location on the posterior pole of fundus of mouse C57BL/6 (purchased from SLC) to destroy the Bruch's membrane, which enabled infiltration of inflammatory cells from the choroid as well as creation of air bubbles subretinally.

A 33 G needle was then inserted from pars plana. 0.5 µl of $4 \times 10^7$ ml thioglycollate elicited peritoneal macrophage and 1 µg, 5 µg, or 50 µg of the benzoic acid of the invention were subretinally injected. For the control, the benzoic acid of the invention was not injected (0 µg).

The subretinal area was observed and subretinal scar region was measure 7 days after injection of the macrophage and the benzoic acid of the invention described above. The results are shown in FIG. 2.
(Results)

Figure 2A:
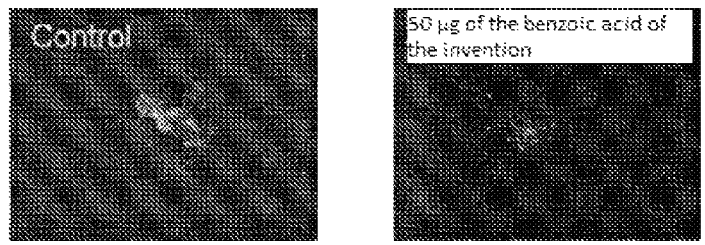
FIGS. 2A-2B are graphs showing the results of studying the effect of inhibiting subretinal scar formation when the benzoic acid of the invention is injected in murine subretinal scar model production.
Figure 2B:
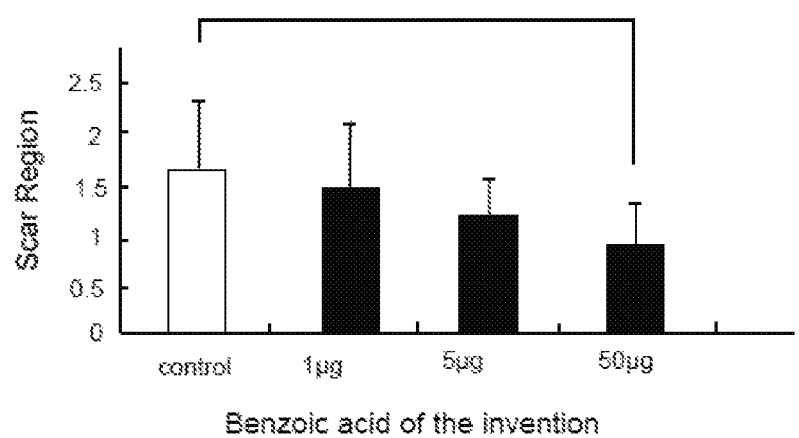

As shown in FIG. 2A, formation of a scar was inhibited when 50 µg of the benzoic acid of the invention was injected in comparison to the control. Further, as shown in FIG. 2B, the scar region (fibrillation region) narrows as the amount of injection of the benzoic acid of the invention increases. Thus, it was revealed that formation and atrophy of subretinal scars can be inhibited by the benzoic acid of the invention.

Example 3

Drug Formulation Example (Drug Formulation Example 1) Instillation

In 100 ml

| | |
|---|---|
| Benzoic acid of the invention | 100 mg |
| Sodium chloride | 800 mg |
| Polysorbate 80 | appropriate amount |
| Disodium hydrogen phosphate | appropriate amount |
| Sodium dihydrogen phosphate | appropriate amount |
| Sterile purified water | appropriate amount |

The benzoic acid of the invention and the other components described above are added to sterile purified water. The solution is thoroughly mixed to prepare an instillation. It is possible to prepare an instillation with a concentration of 0.05% (W/V), 0.3% (W/V), 0.5% (W/V), or 1% (W/V) by changing the amount of the benzoic acid of the invention or the like that is added.

(Drug Formulation Example 2) Ophthalmic Ointment

In 100 g

| | |
|---|---|
| Benzoic acid of the invention | 0.3 g |
| Liquid paraffin | 10.0 g |
| White petrolatum | appropriate amount |

The benzoic acid of the invention is added to homogeneously-melted white petrolatum and liquid paraffin. The mixture is thoroughly mixed and then gradually cooled to prepare an ophthalmic ointment. It is possible to prepare an ophthalmic ointment with a concentration of 0.05% (W/W), 0.1% (W/W), 0.5% (W/W), or 1% (W/W) by changing the amount of the benzoic acid of the invention or the like that is added.

(Drug Formulation Example 3) Tablet

In 100 mg

| Benzoic acid of the invention | 1 mg |
|---|---|
| Lactose | 66.4 mg |
| Corn starch | 20 mg |
| Calcium carboxymethyl cellulose | 6 mg |
| Hydroxypropyl cellulose | 6 mg |
| Magnesium stearate | 0.6 mg |

The benzoic acid of the invention, corn starch and lactose are mixed in a mixer. Calcium carboxymethyl cellulose and hydroxypropyl cellulose are added to the mixture for granulation. The particle size of the resulting granules is adjusted after drying. Magnesium stearate is added to and mixed with the adjusted granules and the mixture is made into tablets with a tableting machine. Further, it is possible to prepare tablets with the content of 0.1 mg, 10 mg, or 50 mg in 100 mg by changing the amount of the benzoic acid of the invention or the like that is added.

INDUSTRIAL APPLICABILITY (E)-4-(2-{3-[(1H-pyrazole-1-yl)methyl]-5,5,8,8-tetramethyl-5,6,7,8-tetrahydronaphthalene-2-yl}vinyl)benzoic acid, an ester thereof, or a salt thereof, which is an effective ingredient of the inhibitor for a retinochoroidal disorder of the present invention, is useful as an inhibitor for retinochoroidal disorders, particularly as an inhibitor for the formation and atrophy of a retinochoroidal scar, by strongly inhibiting collagen contraction in a retinal pigment epithelial cell, fibroblast, glial cell or the like in the retinochoroid.

The invention claimed is:

1. A method of inhibiting or reducing scar formation in the retina and/or choroid of a subject having uveitis, comprising administering to said subject palovarotene ((E)-4-(2-{3-[(1H-pyrazole-1-yl)methyl]-5,5,8,8-tetramethyl-5,6,7,8-tetrahydronaphthalene-2-yl}vinyl) benzoic acid), an ester thereof, or a salt thereof, in an amount effective to inhibit or reduce scar formation.

2. The method of claim 1, wherein said scar formation on the retina and/or choroid is caused by inflammation, infection, or surgery in an ophthalmic tissue.

3. The method of claim 2, wherein said scar formation on the retina and/or choroid is caused by infection.

4. The method of claim 1, wherein said administering comprises administering by instillation.

5. The method of claim 1, wherein said palovarotene is in the form of an ointment, injection, granule, fine granule, powder, syrup, liquid formulation, suspension, emulsion, percutaneous absorption agent, or instillation.

6. The method of claim 5, wherein said ointment is an ophthalmic ointment.

7. The method of claim 6, wherein the concentration of said palovarotene in the ophthalmic ointment administered to said subject is from 0.0001% to 3% (w/w).

8. The method of claim 4, wherein said palovarotene is in the form of an instillation.

9. The method of claim 8, wherein the concentration of said palovarotene in the instillation is from 0.00001% to 3% (w/v).

10. The method of claim 1, wherein said palovarotene is administered to said subject in one or more daily doses.

11. The method of claim 6, wherein the ophthalmic ointment comprises a solubilizer.

12. The method of claim 11, wherein the solubilizer is selected from the group consisting of polysorbate 80, polyoxylethylene hydrogenated castor oil 60, and macrogol 4000.

13. The method of claim 12, wherein the solubilizer is polysorbate 80.

14. The method of claim 6, wherein the concentration of said palovarotene in the ophthalmic ointment is 0.05% (W/W), 0.1% (W/W), 0.5% (W/W), or 1% (W/W).

15. The method of claim 8, wherein the instillation comprises a solubilizer.

16. The method of claim 15, wherein the solubilizer is selected from the group consisting of polysorbate 80, polyoxylethylene hydrogenated castor oil 60, and macrogol 4000.

17. The method of claim 16, wherein the solubilizer is polysorbate 80.

18. The method of claim 8, wherein the concentration of said palovarotene in the instillation is 0.05% (W/V), 0.3% (W/V), 0.5% (W/V), or 1% (W/V).

* * * * *